United States Patent
Weissman

(10) Patent No.: US 7,820,048 B2
(45) Date of Patent: Oct. 26, 2010

(54) METHOD AND SYSTEM FOR TREATING ORGANICALLY CONTAMINATED WASTE WATER

(76) Inventor: Roni Weissman, 117 Hefer Road, P.O. Box 8564, ShaAr Hefer (IL) 42920

( * ) Notice: Subject to any disclaimer, the term of this patent is extended or adjusted under 35 U.S.C. 154(b) by 383 days.

(21) Appl. No.: 12/083,097

(22) PCT Filed: Oct. 15, 2006

(86) PCT No.: PCT/IL2006/001172

§ 371 (c)(1),
(2), (4) Date: Apr. 4, 2008

(87) PCT Pub. No.: WO2007/039910

PCT Pub. Date: Apr. 12, 2007

(65) Prior Publication Data

US 2009/0255870 A1    Oct. 15, 2009

Related U.S. Application Data

(60) Provisional application No. 60/723,986, filed on Oct. 6, 2005.

(51) Int. Cl.
*C02F 3/00* (2006.01)

(52) U.S. Cl. .............. 210/619; 210/622; 210/623; 210/195.1; 210/196; 210/197; 210/198.1

(58) Field of Classification Search ............ 210/619, 210/622, 623, 195.1, 196, 197, 198.1
See application file for complete search history.

(56) References Cited

U.S. PATENT DOCUMENTS

| | | | | |
|---|---|---|---|---|
| 4,537,678 A | * | 8/1985 | Thissen | 210/150 |
| 5,256,570 A | | 10/1993 | Clyde | |
| 6,679,993 B1 | * | 1/2004 | Charuckyj et al. | 210/616 |

FOREIGN PATENT DOCUMENTS

| KR | 2001045253 A | * | 6/2001 |
|---|---|---|---|
| WO | WO 2007/039910 | | 4/2007 |

OTHER PUBLICATIONS

International Preliminary Report on Patentability Dated Jan. 22, 2009 From the International Bureau of WIPO Re.: Application No. PCT/IL2006/001172.

* cited by examiner

*Primary Examiner*—Chester T Barry

(57) ABSTRACT

A method and system for treating organically contaminated waste water for reuse, by: introducing the waste water into a sedimentation tank to remove a significant portion of the organic contaminants; circulating the waste water from the sedimentation tank to an anoxic mixing chamber for denitrifying the waste water; circulating the waste water from the anoxic mixing chamber to a rotary biological contactor to nitrify the waste water by aeration, and to assimilate organic materials therein by bringing the waste water into contact with a biological medium, to thereby output nitrified waste water; and recirculating a portion of the nitrified waste water outputted from the rotary biological contactor back to the anoxic mixing chamber to enhance the nitrifying and denitrifying of the waste water.

10 Claims, 1 Drawing Sheet

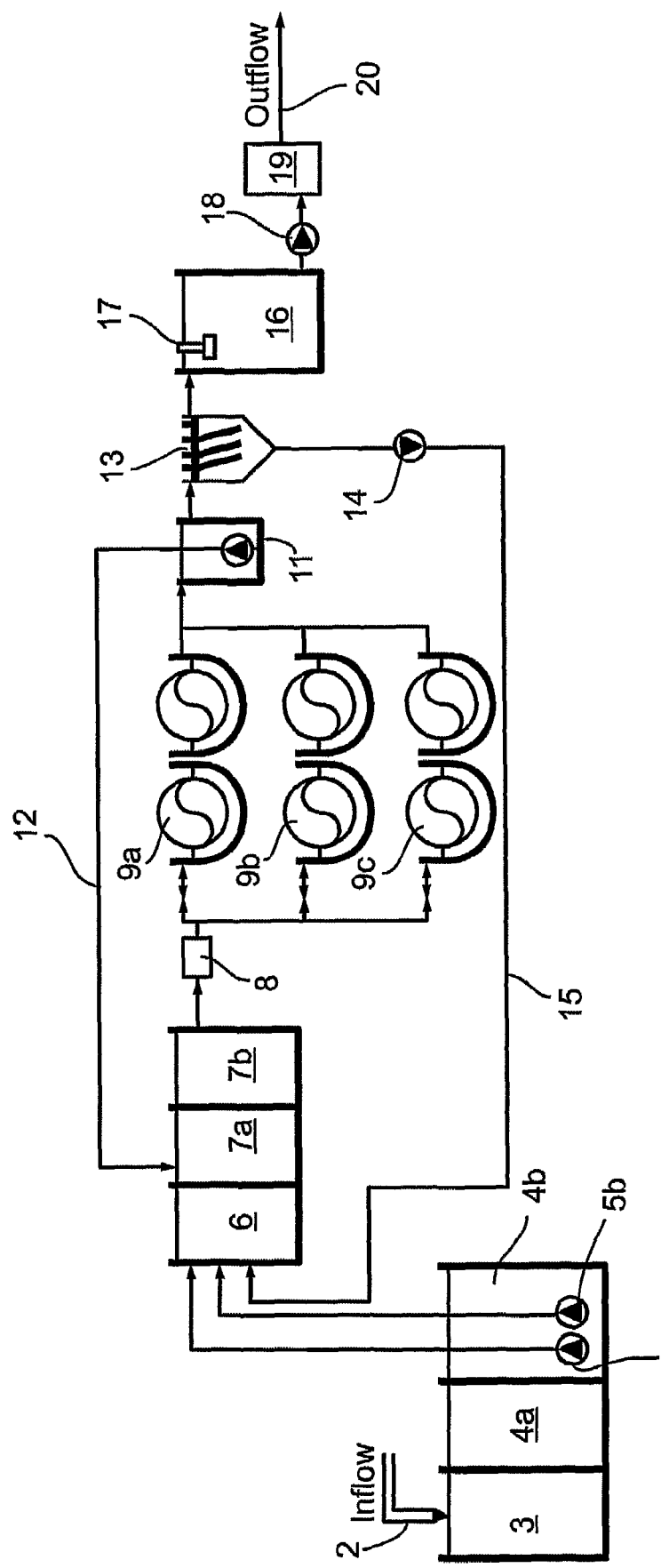

METHOD AND SYSTEM FOR TREATING ORGANICALLY CONTAMINATED WASTE WATER

RELATED APPLICATIONS

This Application is a National Phase of PCT Patent Application No. PCT/IL2006/001172 having International filing date of Oct. 15, 2006, which claims the benefit of U.S. Provisional Patent Application No. 60/723,986 filed on Oct. 6, 2005. The contents of the above Applications are all incorporated herein by reference.

FIELD AND BACKGROUND OF THE INVENTION

The present invention relates to a method and system for treating organically contaminated waste water for reuse. The invention is particularly useful in waste water treating systems wherein the space available for such a treatment system is limited and/or where the concentration of the organic contaminants is relatively high.

Many systems are known, and are in present use, for treating organically contaminated waste water in order to permit reuse of the waste water, e.g. for agricultural purposes or the like. One known system includes a sedimentation tank for receiving the waste water and for removing a significant portion of the organic contaminants; an anoxic mixing chamber for denitrifying the waste water; and a rotary biological contactor for nitrifying the waste water by aeration, and for assimilating organic materials therein by bringing the waste water into contact with a biological medium. The so-treated waste water may then be conducted to a clarifier, chlorinator, filter, or the like to further purify the water.

The known systems of the type including rotary biological contactors generally require considerable space and/or residence time, to treat the waste water sufficiently to permit its reuse when an advanced denitrification process is required, e.g. for irrigation purposes, and are therefore not suitable for the onsite treatment of waste water in residential and small commercial applications in hydraulic sensitive areas.

OBJECT AND BRIEF SUMMARY OF THE PRESENT INVENTION

A broad object of the present invention is to provide a method, and also a system, for treating organically contaminated waste water for reuse, which method and system do not require substantial space and/or substantial resident time, and therefore are more suitable for residential and small commercial applications.

According to one aspect of the present invention, thus provided a method of treating organically contaminated waste water for reuse, comprising: introducing the waste water into a sedimentation tank to remove a significant portion of the organic contaminants; circulating the waste water from the sedimentation tank to an anoxic mixing chamber for denitrifying the waste water; circulating the waste water from the anoxic mixing chamber to a rotary biological contactor to nitrify the waste water by aeration, and to assimilate organic materials therein by bringing the waste water into contact with a biological medium, to thereby output nitrified waste water; and recirculating a portion of the nitrified waste water outputted from the rotary biological contactor back to the anoxic mixing chamber to enhance the nitrifying and denitrifying of the waste water.

According to further features in the preferred embodiment of the invention described below, the portion of the nitrified waste water recirculated back to the anoxic mixing chamber is recirculated from a second anoxic mixing chamber receiving the nitrified waste water outputted from the rotary biological contactor.

According to a still further preferred feature in the embodiment described below, the waste water is circulated from the second anoxic mixing chamber to a lamella separator to separate sludge from the waste water.

According to a still further preferred feature in the described preferred embodiment, the waster water is circulated from the sedimentation chamber to a sludge holding tank before circulated to the first-mentioned anoxic mixing chamber; and the sludge from the lamella separator is pumped to the first-mentioned anoxic mixing chamber.

In the described preferred embodiment, the significant portion of the solids removed in the sedimentation tank is at least 35%, preferably 35-45%.

According to another aspect of the present invention, thus provided a system for treating organically contaminated waste water for reuse, comprising: a sedimentation tank for receiving the waste water and for removing a significant portion of the organic contaminants therein; an anoxic mixing chamber for receiving waste water from the sedimentation tank and for nitrifying the waste water; a rotary biological contactor for receiving the waste water from the anoxic mixing chamber, for nitrifying the waste water by aeration, and for assimilating organic material in the waste water; and a recirculation pump for recirculating a portion of the nitrified waste water outputted from the rotary biological contactor back to the anoxic mixing chamber to enhance the nitrifying and denitrifying of the waste water.

As will be described more particularly below, the method and system of the present invention require substantially less space than a conventional system of this type, and therefore are more suitable for use by residential and small commercial applications than the conventional system of this type.

Further features and advantages of the invention will be apparent from the description below.

BRIEF DESCRIPTION OF THE DRAWINGS

The attached single FIGURE of drawing schematically illustrates a system constructed in accordance with the present invention for treating organically contaminated waste water for reuse, in accordance with the method of the present invention.

It is to be understood that the foregoing drawing, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiment described is for purposes of example only, and that the invention is capable of being embodied in other forms and applications than described herein.

DESCRIPTION OF A PREFERRED EMBODIMENT

Overall System

As indicated earlier, the system illustrated in the accompanying drawing is particularly useful as an onsite waste water treatment system for use in residential and small commercial applications, since such a system can be built in a relatively small space at a relatively low cost. For example, the illustrated system can be constructed to process from 50 to 2700 gallons per day of raw waste water for reuse, e.g. for irrigation purposes. It is therefore particularly suitable for rural areas, or for places without central sewage systems.

In the system illustrated in the accompanying drawing, the waste water to be treated is applied via an inlet conduit 2 into a sedimentation tank 3 to remove a significant portion of the organic contaminants. Sedimentation tank 3 communicates with a plurality of equalization tanks 4a, 4b to equalize the flow through the system.

Equalization tank 4b includes equalization pumps 5a, 5b which pump the wastewater to a sludge holding tank 6 which communicates with a plurality of anoxic mixing chambers 7a, 7b to denitrify the waste water. The waste water from anoxic mixing chamber 7b is conducted via a flow divider 8 to a plurality of rotary biological contactors 9a, 9b, 9c, of any known design. Such rotary biological contactors generally consist of a series of disks mounting on a shaft which is driven so that the disks rotate at right angles to the flow of the waste water. The disks are usually made of plastic and are contained in a trough so that about 40% of their area is immersed. The rotary biological contactors thus nitrify the waste water by aeration, and assimilate organic materials therein by bringing the waste water into contact with a biological medium. Thus, the output of the rotary biological contactors is nitrified waste water.

The outputs from the rotary biological contactors 9a-9c are fed to another anoxic mixing chamber 10 which further denitrifies the waste water. A portion of the waster water from anoxic mixing chamber 10 is recirculated via pump 11 and recirculation line 12, back to anoxic mixing chamber 7a. This recirculation of the waste water from anoxic mixing chamber 10 back to anoxic mixing chamber 7a has been found to substantially enhance the nitrifying and denitrifying of the waste water.

The waste water from anoxic mixing chamber 10 is gravity-fed to a lamella separator 13. Such separators are well known and generally include a plurality of inclined parallel plates and a sludge hopper at the bottom. The waste water flows upwardly through the plates, whereupon the solid particles settle on the inclined plates and slide down into the sludge hopper at the bottom. The sludge is pumped via a sludge pump 14 and a line 15 back to the sludge holding tank 6, whereas the waste water is gravity-fed to a reservoir 16. Reservoir 16 may include a chlorinator 17 for chlorinating the water. The water in reservoir 16 may be pumped, as required, by pump 18 via a filter 19 and out flow conduit 20 to the irrigation devices (not shown) when the so-treated water is used for irrigation purposes.

Example of a Preferred Design

Following is an example of a system design able to treat 500 to 2,700 gallons per day of raw waste water.

If it is desired to effect a significant saving in the total surface area of the disks in the rotary biological contactors 9a-9c, it is recommended that the sedimentation tank 3 also include the equalization tanks 4a, 4b so as to effect a removal of 35-45% of the organic contaminants. It is recommended that a Hydraulic Retention Time (HRT) of 12-14 hours be used and that a reinforced concrete construction be used.

The first anoxic mixing chamber 6 may be relatively small, with not more than 10 minutes HRT. Gentle mixing should be used in this chamber under controlled anoxic conditions, to perform an efficient denitrifying stage. The total inlet flow for operational volume calculation should take into account the hourly waste water inlet flow rate plus the hourly adopted internal recycling.

The rotary biological contactors 9a-9c are gravity-flowing systems and are characterized by about 5,400 sq.ft. (500 m$^2$) of active attached biomass layers for every contactor of about 6.6 feet (2.0 meters) in length. Their organic contaminant removal rate is in the order 1.40 to 2.60 gallons/sq.ft./day, which means 16.5 to 21.0 pounds organic contaminants/day for every contactor. The number of contactor units required depends on the daily biological loading of the organic contaminants for the particular application.

The recirculation rate from the downstream anoxic mixing chamber 10 to the upstream mixing chamber 7a, via pump 11 and recycling line 12, depends on the concentration of the organic contaminants, and particularly on the nitrates, in the waste water inletted into the system, via inflow pipe 2, and the maximum permitted concentration of organic contaminants and nitrates produced at the outflow pipe 20 for the particular application. As one example, the recycling rate may be in the order of 10 to 12 times the inletted waste water hourly flow rate.

The downstream anoxic mixing chamber 10 is also gravity-fed from the rotary biological contactors 9a-9c. Besides denitrification, mixing chamber 10 also effects phosphorous removal. Preferably, the hydraulic retention time (HRT) in the downstream anoxic mixing chamber 10 is not more than 10-20 minutes, and is characterized by gentle mixing and controlled addition of chemicals for phosphorus precipitation.

The flow of the waste water from the downstream anoxic mixing chamber 10 to the lamella separator 13 is effected by top overflow and is characterized by an average upward velocity in the order of 1.0 to 1.3 mm/sec, operating with a Reynolds Number in the order of 500 to 700. The sheets in lamella separator 13 are preferably of polypropylene.

The sludge collected at the bottom of lamella separator 13 is pumped, via sludge pump 14 and line 15, back to the sludge holding tank 6 for collection in that tank. The sludge accumulating in tank 6 may be periodically removed. The top overflow liquid from lamella separator 13 into reservoir 16 should normally have no more than 5 mg/L suspended solids. Preferably, it is chlorinated by chlorinator 17 at the time it is received within reservoir 16. It is stored in reservoir 16 until needed for irrigation, or for other appropriate reuse of the water. If desired, it can be subjected to a filtering operation, as shown at 19, before used for irrigation or other purposes, such as to contain suspended solids of less than five microns. The solids filtered out can be discarded or returned to sedimentation chamber 3 for backwashing and then discarding.

If desired for a particular application, a final disinfecting stage could be added using chlorination or other ultraviolet technology.

The following table sets forth one example of parameter design values which can be used with respect to the rotary biological contactors 9a-9c in the above-described system for one particular application:

| Parameter | Design Values |
| --- | --- |
| Pretreatment | Septic, Equalization Chamber (tanks 3, 4a, 4b) |
| Attached Biota Efficiency | 1.60 tp 2.40 gBOD/sq. ft.-day |
| Biota Layer Thickness | 2 to 6 mm |

-continued

| Parameter | Design Values |
|---|---|
| Rotation Velocity | 4.0 to 4.5 rpm |
| Power Requirements | 1.1 KW per every two baths of 6.6 ft. length |
| Number of Discs per Bath | 70 to 82 |
| MLSS concentration | Exceptionally high. Could be 40,000 mg/L and more |
| Sludge age | 30 to 45 days - Could be 90 days |
| F/M ration | Exceptionally low |
| Hydraulic Retention Time (HRT) | 1.8 to 2.5 hours |
| Residuals generated | 0.60 yo 0.71 lb TSS/lbBOD removed |
| Sludge Removal | Twice to thrice/day from settler bottom |
| Specific Energy Consumption | 0.21 to 0.60 kWh/kgBOD remobed |

Advantages in the Described Systems

As indicated earlier, the recirculation of the waste water from the anoxic mixing chamber 10 back to the anoxic mixing chamber 7a enhances the nitrifying and denitrifying of the waste water. The rotary biological contactors 9a-9c provide a plentiful supply of oxygen, at least 150% in excess of required oxygen, to aerate the waste water and to completely oxidize the organic contaminants as well as the nitrates, nitrites, and ammonium. The recirculation of the sludge from lamella separator 13 back to the sludge holding tank 6 via sludge pump 14 and line 15, reduces or eliminates "sludge bulking", namely the appearance of a disagreeable floating layer at the top of the waste water being treated.

In addition, except for the equalization pumps 5a 5b, the denitrification pump 11, and the sludge pump 14, the transfer of the waste water form one tank to the next may be effected by gravity feed, thereby substantially reducing the overall installation costs as well as the maintenance costs. In addition, the system has been found to be sufficiently environmentally-friendly with respect to ground-water contamination, odors, and the like, such that it can be installed relatively close to residential buildings.

While the invention has been described with respect to one preferred embodiment, it will be appreciated that this is set forth merely for purposes of example, and that many other variations, modifications and applications of the invention will be apparent.

What is claimed is:

1. A method of treating organically contaminated waste water for reuse, comprising:
   introducing the waste water into a sedimentation tank to remove a significant portion of the organic contaminants;
   circulating the waste water from the sedimentation tank to an anoxic mixing chamber for denitrifying the waste water;
   circulating the waste water from the anoxic mixing chamber to a rotary biological contactor to nitrify the waste water by aeration, and to assimilate organic materials therein by bringing the waste water into contact with a biological medium, to thereby output nitrified waste water;
   and recirculating a portion of the nitrified waste water outputted from the rotary biological contactor back to the anoxic mixing chamber to enhance the nitrifying and denitrifying of the waste water.

2. The method according to claim 1, wherein said portion of the nitrified waste water recirculated back to the anoxic mixing chamber is recirculated from a second anoxic mixing chamber receiving the nitrified waste water outputted from the rotary biological contactor.

3. The method according to claim 2, wherein the waste water is circulated from said second anoxic mixing chamber to a lamella separator to separate sludge from the waste water.

4. The method according to claim 3, wherein the waste water is circulated from the sedimentation chamber to a sludge holding tank before circulated to the first-mentioned anoxic mixing chamber; and wherein the sludge from the lamella separator is pumped to said first-mentioned anoxic mixing chamber.

5. The method according to claim 1, wherein said significant portion of the organic contaminant removed in the sedimentation tank is at least 35% of the waste water introduced into said sedimentation tank.

6. A system for treating organically contaminated waste water for reuse, comprising:
   a sedimentation tank for receiving the waste water and for removing a significant portion of the organic contaminants therein;
   an anoxic mixing chamber for receiving waste water from the sedimentation tank and for nitrifying the waste water;
   a rotary biological contactor for receiving the waste water from the anoxic mixing chamber, for nitrifying the waste water by aeration, and for assimilating organic material in the waste water;
   and a recirculation pump for recirculating a portion of the nitrified waste water outputted from the rotary biological contactor back to the anoxic mixing chamber to enhance the nitrifying and denitrifying of the waste water.

7. The system according to claim 6, wherein said system further comprises a second anoxic mixing chamber receiving the nitrified waste water outputted from the rotary biological contactor, said recirculating pump recirculating waste water from said second anoxic mixing chamber back to the first-mentioned anoxic mixing chamber.

8. The system according to claim 7, wherein said system further comprises a lamella separator receiving waste water from said second anoxic mixing chamber to separate sludge from the waste water.

9. The system according to claim 8, wherein said system further comprises a sludge recirculating pump for recirculating sludge from said lamella separator to the first-mentioned anoxic mixing chamber.

10. The system according to claim 8, wherein said system further comprises a chlorinator for chlorinating the output of the lamella separator.

* * * * *